US012692534B2

(12) United States Patent
Maruyama et al.

(10) Patent No.: US 12,692,534 B2
(45) Date of Patent: Jul. 28, 2026

(54) PREANALYSIS TREATMENT METHOD FOR SAMPLE, AND SAMPLE PRETREATMENT SYSTEM

(71) Applicant: Hitachi, Ltd., Tokyo (JP)

(72) Inventors: Masashi Maruyama, Tokyo (JP); Hirotaka Sakuma, Tokyo (JP); Eric Ofosu-Twum, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 1147 days.

(21) Appl. No.: 17/713,621

(22) Filed: Apr. 5, 2022

(65) Prior Publication Data

US 2022/0317130 A1     Oct. 6, 2022

(30) Foreign Application Priority Data

Apr. 6, 2021    (JP) ................................. 2021-064879

(51) Int. Cl.
*C12Q 1/37*        (2006.01)
*G01N 1/38*        (2006.01)
*G01N 33/68*      (2006.01)

(52) U.S. Cl.
CPC ................. *C12Q 1/37* (2013.01); *G01N 1/38* (2013.01); *G01N 33/6848* (2013.01)

(58) Field of Classification Search
CPC ......... G01N 33/6848; G01N 1/38; C12Q 1/37
See application file for complete search history.

(56) References Cited

U.S. PATENT DOCUMENTS

| | | | |
|---|---|---|---|
| 11,415,579 B2 | 8/2022 | Mann et al. | |
| 2002/0037532 A1* | 3/2002 | Regnier ............. | G01N 33/6851 435/7.1 |
| 2007/0037242 A1 | 2/2007 | Ji et al. | |

FOREIGN PATENT DOCUMENTS

| | | | |
|---|---|---|---|
| CN | 106632877 A | * | 5/2017 |
| JP | 2007-44043 A | | 2/2007 |
| JP | 2019-526792 A | | 9/2019 |

OTHER PUBLICATIONS

Vale, G et al. An assessment of the ultrasonic probe-based enhancement of protein cleavage with immobilized trypsin. Proteomics. 2011. 11: 3866-3876. (Year: 2011).*
Zwyssig, A et al. Protein reduction and dialysis-free work-up through phosphines immobilized on a magnetic support: TCEP-functionalized carbon-coated cobalt nanoparticles. Chem. Eur. J. 2017. 23: 8585-8589. (Year: 2017).*
Zhang et al. CN 106632877. Machine Translation. May 10, 2017. (Year: 2017).*
Jeng, J et al. Using high-concentration trypsin-immobilized magnetic nanoparticles for rapid in situ protein digestion at elevated temperature. Rapid Communications in Mass Spectrometry. 2007. 21: 3060-3068. (Year: 2007).*
Tzanavaras, PD et al. On-line cleavage of disulfide bonds by soluble and immobilized tris-(2-carboxyethyl)phosphine using sequential injection analysis. Talanta. 2012. 96: 21-25. (Year: 2012).*
Japanese language Office Action issued in Japanese Application No. 2021-064879 dated Jan. 7, 2025 with English translation (6 pages).
Millan-Martin S et al. "Inter-laboratory study of an optimised peptide mapping workflow using automated trypsin digestion for monitoring monoclonal antibody product quality attributes", Analytical and Bioanalytical Chemistry, Jul. 25, 2020, pp. 6833-6848, vol. 412, (16 pages).

* cited by examiner

*Primary Examiner* — David W Berke-Schlessel
*Assistant Examiner* — Susan E. Fernandez
(74) *Attorney, Agent, or Firm* — Crowell & Moring LLP

(57)                ABSTRACT

Objects of the disclosure are to provide a preanalysis treatment method for a sample, which can reduce mixing of a reagent into the sample, and to provide a sample pretreatment system capable of performing the preanalysis treatment method. An aspect of the present embodiment is a preanalysis treatment method for a sample, which includes a step A of mixing the sample and a reagent A containing a support and a reducing agent immobilized on the support, a step B of mixing the sample and a reagent B containing a support and an enzyme immobilized on the support, a step X-A of, after the step A, separating the reagent A and a supernatant from each other, and a step X-B of, after the step B, separating the reagent B and a supernatant from each other.

5 Claims, 4 Drawing Sheets

F I G . 1

STEP A: ADD REAGENT A

STEP B: ADD REAGENT B

STEPS X-A AND X-B: SEPARATE
SUPERNATANT FROM REAGENTS A AND B

STEP A: ADD REAGENT A

STEP C: ADD REAGENT C

STEP B: ADD REAGENT B

STEPS X-A, X-B, AND X-C: SEPARATE
SUPERNATANT FROM REAGENTS A, B, AND C

F I G . 3
STEPS A AND B: ADD REAGENTS A AND B
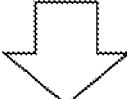
STEPS X-A AND X-B: SEPARATE
SUPERNATANT FROM REAGENTS A AND B

PREANALYSIS TREATMENT METHOD FOR SAMPLE, AND SAMPLE PRETREATMENT SYSTEM

BACKGROUND OF THE INVENTION

1. Field of the Invention

The present invention relates to a preanalysis treatment method for a sample, and a sample pretreatment system.

2. Description of the Related Art

Analyses of peptides and proteins by liquid chromatography-mass spectrometry (LC-MS) are important in a variety of fields such as foods, medicines, and diagnoses. When LC-MS analyses of peptides and proteins are performed, fragmentation with use of enzymatic digestion or the like is generally needed. According to conventional technology, a sample is fragmented by allowing an enzyme solution or the like to act on the sample after its reduction or its alkylation. With this method, however, residues of a reagent used in the reduction or alkylation, residues of the enzyme, fragments of the enzyme, and the like mix into the sample, so that subsequent steps may adversely be affected.

In the meanwhile, a method that uses a column with an enzyme immobilized therein has been proposed (see, for example, JP-2007-44043-A (referred to as Patent Document 1, hereinafter)). Further, a method that uses an immobilized enzyme or the like as a dispersion has also been proposed (see, for example, Analytical and Bioanalytical Chemistry volume 412, pages 6833-6848 (2020) (referred to as Patent Document 2, hereinafter)).

SUMMARY OF THE INVENTION

The invention described in Patent Document 1, however, involves a potential problem that a performance deterioration and/or cross contamination may occur through repeated use of the column. In the method described in Patent Document 2, the dispersion that contains the immobilized enzyme can be used in a disposable system, but subsequent steps may adversely be affected due to mixing of residues of a reagent used in reduction or alkylation.

The present disclosure therefore has as an object thereof the provision of a preanalysis treatment method for a sample, which can reduce mixing of a reagent into the sample, in pretreatment of the sample.

The present disclosure also has as another object thereof the provision of a sample pretreatment system capable of performing the preanalysis treatment method that can achieve the above-mentioned object.

Solution to Problems

Aspects of this embodiment are as follows.

A preanalysis treatment method for a sample containing a peptide or a protein, which includes a step A of mixing the sample and a reagent A containing a support and a reducing agent immobilized on the support, a step B of mixing the sample and a reagent B containing a support and an enzyme immobilized on the support, a step X-A of, after the step A, separating the reagent A and a supernatant from each other, and a step X-B of, after the step B, separating the reagent B and a supernatant from each other.

A sample pretreatment system capable of performing the above-described preanalysis treatment method, which includes a control unit, a sample tube rack, a sample tube heating/shaking unit, a reagent dispensing unit, and a supernatant recovering unit.

Compared with the conventional preanalysis treatment methods, the application of the preanalysis treatment method according to the embodiment can reduce the mixing of the reagent or reagents into the sample. Further, this preanalysis treatment method facilitates to create disposable systems, thereby making it possible to also suppress cross contamination.

BRIEF DESCRIPTION OF THE DRAWINGS

FIG. 1 is a process flow diagram illustrating an aspect of a preanalysis treatment method according to an embodiment;

FIG. 3 is a process flow diagram illustrating an aspect of the preanalysis treatment method according to the embodiment.

DESCRIPTION OF THE PREFERRED EMBODIMENT

Figure 2:
FIG. 2 is a process flow diagram illustrating an aspect of the preanalysis treatment method according to the embodiment.
Figure 2:
Figure 2:
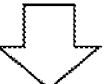
Figure 2:
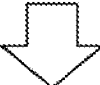

An aspect of the present embodiment is a preanalysis treatment method for a sample containing a peptide or a protein, which includes a step A of mixing the sample and a reagent A containing a support and a reducing agent immobilized on the support, a step B of mixing the sample and a reagent B containing a support and an enzyme immobilized on the support, a step X-A of, after the step A, separating the reagent A and a supernatant from each other, and a step X-B of, after the step B, separating the reagent B and a supernatant from each other.

By the above-described aspect, it is possible to reduce the mixing of the reagent or reagents into the sample subjected to the preanalysis treatment method, because the reagents, such as the reagents A and B, contain the supports and the reducing agent and the enzyme are immobilized on the supports, so that the separation of the reagents A and B and the supernatants with the sample contained therein after the performance of the step A and the step B is facilitated in the step X-A and the step X-B. Further, by creating this preanalysis treatment method as a disposable system, it is also possible to suppress cross contamination which occurs, for example, through repeated use of columns.

An aspect of the present invention is a sample pretreatment system that can perform the above-described preanalysis treatment method. The sample pretreatment system can perform the above-described preanalysis treatment method by including, for example, a control unit, a sample tube rack, a sample tube heating/shaking unit, a reagent dispensing unit, and a supernatant recovering unit.

The aspects of the present embodiment will hereinafter be described in detail. In the following description, the embodiment will be described with reference to the drawings as needed. The following description presents detailed examples of contents of the embodiment. Therefore, the present embodiment should not be limited to the following description, and various changes and alterations can be made by persons skilled in the art within the scope of the technical concept disclosed herein. Throughout all the drawings for describing this embodiment, those having the same function will be identified by the same reference sign, and its repeated description may be omitted.

[Preanalysis Treatment Method]

The preanalysis treatment method according to the embodiment is a preanalysis treatment method for a sample containing a peptide or a protein, and includes a step A of mixing the sample and a reagent A containing a support and a reducing agent immobilized on the support, a step B of mixing the sample and a reagent B containing a support and an enzyme immobilized on the support, a step X-A of, after the step A, separating the reagent A and a supernatant from each other, and a step X-B of, after the step B, separating the reagent B and a supernatant from each other. The preanalysis treatment method according to the embodiment uses the reagents with the reducing agent and the enzyme immobilized on the supports, so that their separation is easy.

No particular limitation is imposed on the sample to which the preanalysis treatment method is applied, insofar as it contains a peptide or protein. In general, however, the sample contains at least one of the peptide and protein. The at least one of the peptide and protein is, for example, an antibody. In the preanalysis treatment method, denaturation and fragmentation of the peptide or protein are performed. The term "denaturation" as used here means to subject disulfide bonds in molecules to reductive cleavage or to modify higher order structures in molecules, so that a higher digestion efficiency is provided. On the other hand, the term "digestion" as used here means to cleave covalent bonds in molecules, so that the peptide or protein is fragmented. Digestion is performed for increasing the efficiency of detection by LC-MS or for a like purpose. In the preanalysis treatment method of the embodiment, denaturation can be performed with the reagent A, and digestion or fragmentation can be performed with the reagent B.

Analyses of digested or fragmented peptides and proteins have been performed conventionally. The preanalysis treatment method of the embodiment can contribute to speeding up of such analyses as the time required for pretreatment is short. In addition, the reagents used for the denaturation and digestion are immobilized, and their recovery is hence easy. Accordingly, the mixing of the reagents into the digested sample can be suppressed, and improvements are expected in accuracy of analysis.

As the sample to which the preanalysis treatment method is applied, it is preferably in a liquid form from the viewpoint of efficient reactions with the reagents. The sample can be a liquid sample, for example, a body fluid such as blood, urine, perspiration or tear, or a sample other than a body fluid, for example, a sample derived from cells, for example, animal cells, bacterial cells, or plant cells. Examples of the sample derived from the cells include cell extracts, and secretions and cultures in cultivation. The sample may also be a protein-containing reaction mixture in a cell-free protein synthesis, or a reaction mixture available from chemical modification of a protein. The sample may also be a sample the concentration of which has been adjusted by use of a solvent, which will be described subsequently herein, as needed. The sample may also be a sample derived from a human, or a sample derived from a non-human. Examples of the sample derived from the non-human include samples derived from mammals other than human subjects, and samples derived from organisms other than mammals, for example, birds, fish, insects, plants, algae, and bacteria. Examples of the mammals other than human subjects include mice, rats, horses, sheep, swine, goats, and cattle.

The sample to which the preanalysis treatment method is applied may desirably be a sample which has been subjected to appropriate treatment, such as contaminant removal, adsorption treatment, desalting, solvent replacement, dialysis, and/or concentration, as needed.

In the preanalysis treatment method, the reagent A, which contains the support and the reducing agent immobilized on the support, as well as the reagent B, which contains the support and the enzyme immobilized on the support, are used. If desired, the reagent C, which contains the support and the alkylating agent immobilized on the support, may also be used in the preanalysis treatment method. It is to be noted that "the reagent A, which contains the support and the reducing agent immobilized on the support" may hereafter be also referred to as "the reagent A" or "the immobilized reducing agent." Likewise, "the reagent B, which contains the support and the enzyme immobilized on the support" may hereafter be also referred to as "the reagent B" or "the immobilized enzyme." Further, "the reagent C, which contains the support and the alkylating agent immobilized on the support" may hereafter be also referred to as "the reagent C" or "the immobilized alkylating agent."

In conventional denaturation, thiols such as dithiothreitol, cysteine, and glutathione, phosphines such as TCEP (tris(2-carboxyethyl)phosphine hydrochloride), and the like have been generally used as reducing agents for disulfide bonds. Including these reducing agents, no particular limitation is imposed on the reducing agent contained in the reagent A. Preferably, however, the reducing agent contained in the reagent A may contain at least one thiol or phosphine group as a partial structure thereof. When the reagent A is added to the sample and is allowed to react with the sample under appropriate conditions, reductive cleavage of disulfide bonds in target molecules is feasible.

The preanalysis treatment method of the embodiment may also perform alkylation. Alkylation can be performed to suppress disulfide bonds, which have been subjected to reductive cleavage, from undergoing refolding to disulfide bonds through a reverse reaction by oxidative oxidation or the like. As the alkylating agent for use in the alkylation, a nucleophilic reagent such as iodoacetamide or iodoacetic acid can be used in general in the embodiment. Including these alkylating agents, no particular limitation is imposed on the alkylating agent contained in the reagent C. Nonetheless, a nucleophilic reagent that has selectivity to a soft base such as a thiolate is preferred as the alkylating agent to suppress competition with alkylation of amine residues and the like in target molecules.

No particular limitation is imposed on the enzyme contained in the reagent B, insofar as it can digest the peptide or protein in the sample. Protease is a preferred example of the enzyme. The enzyme may preferably contain at least one enzyme selected from trypsin, chymotrypsin, pepsin, Lys-C, Lys-N, and Glu-C.

No particular limitation is imposed on a method for immobilizing the reducing agent, enzyme or alkylating agent in the reagent A, reagent B, or reagent C. For example, an existing technique can be used. The term "immobilize" as used here means to compound the reducing agent, enzyme, or alkylating agent with the support into such a state that the activity of the reducing agent, enzyme, or alkylating agent is maintained in a permissible range, and a method such as chemical bonding or physical adsorption can be used. In the immobilization, the selection of a support, the surface treatment of the support, the selection of a linker, the immobilization method of the linker, the quantitation of an immobilized amount, and the like can be carried out as needed by existing techniques.

Although no particular limitation is imposed on the material of each support, preferred is a material that satisfies requirements such as easy mixability with the sample, readily separability from the sample in a subsequent step, and low nonspecific adsorption property for target molecules of pretreatment in the sample. The support may be made of a single kind of material, may be made of a composite material formed from a plurality of materials, and may have a surface coating or the like. Examples of the surface coating include polysaccharide coatings, hydrophobic polymer coatings, amphoteric polymer coatings, and the like, all of which can function to reduce nonspecific adsorption.

Usable examples of the material of each support include metal oxides such as silica and titania, organic resins such as polystyrene and acrylic resins, polysaccharides such as crosslinked agarose, elementary metals such as metal nano-particles, semiconductors such as semiconductor nano-particles, and the like. Further, a support with magnetism such as superparamagnetism imparted thereto may also be used to facilitate separation in a subsequent step. Examples of a magnetism imparting method include use of a magnetic material, compounding with particles made of a magnetic material, and the like. Examples of the magnetic material include, but are not limited to, magnetic metal oxides such as iron oxide and cobalt oxide. Each support may preferably contain at least one material selected from silica, polystyrene, acrylic resins, polysaccharides, elementary metals, semiconductors, metal oxides, and magnetic metal oxides.

The linker is not limited in kind, length, hydrophobicity/hydrophilicity, and so on. Desirably, however, the linker does not inhibit the activities of the associated reagents. Examples of the liker include oligoethylene glycol, polyethylene glycol, alkyl groups, and the like.

No particular limitation is imposed on the shape of each support. However, the support may desirably present a certain specific shape such as a sphere, because its shape is preferably supposed to ensure the reproducibility of pre-analysis treatment. The support may be porous or nonporous. However, a greater specific surface area tends to lead to higher nonspecific adsorption, so that an appropriate porosity can be selected according to the purpose. No limitation is imposed either on the particle size of the specific surface area. However, a greater particle size tends to facilitate separation in a subsequent step, so that an appropriate particle size can be selected according to the purpose. The support has an average diameter of preferably 0.5 μm to 500 μm, more preferably 1 μm to 100 μm, still more preferably 2 μm to 30 μm. The support tends to facilitate to ensure higher reproducibility as its particle size distribution becomes narrower. However, no limitation is imposed on the particle size distribution, and an appropriate particle size distribution can be selected according to the purpose.

As the supports contained in the reagents A, B, and C, a single kind of support may be used, or different kinds of supports may be used.

The preanalysis treatment method of the embodiment includes the step A of mixing the sample and the reagent A, the step B of mixing the sample and the reagent B, the step X-A of, after the step A, separating the reagent A and the supernatant from each other, and the step X-B of, after step B, separating the reagent B and the supernatant from each other. The preanalysis treatment method of the embodiment may further include a step C of mixing the sample and the reagent C, and a step X-C of, after the step C, separating the reagent C and the supernatant from each other. No particular limitation is imposed on the order in which the step A and the step B are performed. The step A and the step B may be concurrently performed, or one of the steps A and B may be performed first, and the other step may then be performed. Preferably, however, the step A and the step B are concurrently performed, or the step B is performed after the step A is performed. If the step C is performed, the step C may be performed concurrently with the step A, may be performed after the step A and before the step B, or preferably may be performed concurrently with the step B after the step A. Described specifically, examples of the order in which the step A, the step B, and the optionally performed step C are performed include an aspect in which the step A and the step B are concurrently performed, another aspect in which the step B is performed after the step A is performed, a further aspect in which the step B is performed after the step A and the step C are concurrently performed, a still further aspect in which, after the step A is performed, the step C is performed and the step B is then performed, an even further aspect in which, after the step A is performed, the step B and the step C are concurrently performed, and a still even further aspect in which the step A, the step B and the step C are concurrently performed.

The step X-A, the step X-B, and the step X-C are performed after the step A, the step B, and the step C are performed, respectively, and no particular limitation is imposed on the order in which the step X-A, the step X-B, and the step X-C are performed. For example, the step X-A, the step X-B, and the step X-C which is performed if the step C is performed may be concurrently performed, after the step A, the step B, and the optionally performed step C are performed. Alternatively, the step X-A may be performed after the step A is performed, the step X-C may be performed after the step C is performed, and the step X-B may then be performed after the step B is performed.

Figure 1:
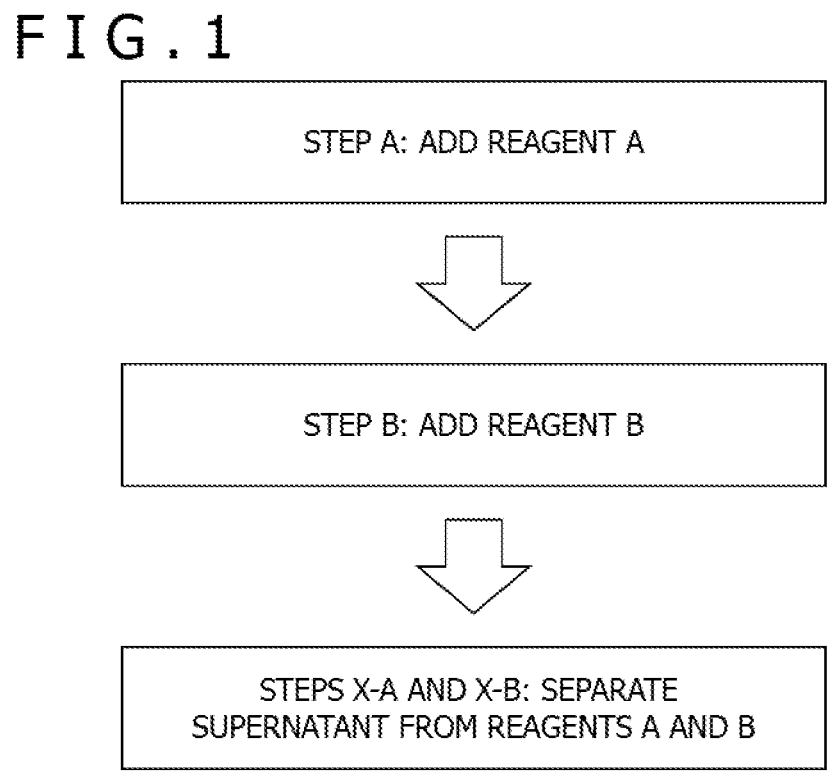

Examples of the aspects of the preanalysis treatment method according to the embodiment will hereinafter be described. For example, there is the aspect in which the step A is performed, the step B is then performed, and the steps X-A and X-B are next performed concurrently (FIG. 1). As an example including the step C, there is the aspect in which the step A is performed, the step C is then performed, the step B is next performed, and after that, the steps X-A, X-B and X-C are performed concurrently (FIG. 2). As an example of performing the steps A and B concurrently, there is the aspect in which the steps A and B are first performed concurrently, and the steps X-A and X-B are then performed concurrently (FIG. 3). As illustrated in FIGS. 1 and 3, the steps A and B may be performed concurrently or separately.

The step C is not necessarily needed if the step B i.e. digestion is performed under such conditions as allowing to disregard the reverse reaction through which disulfide bonds cleaved in the step A undergo refolding to disulfide bonds by oxidative oxidation or the like. Examples of the case which does not need to perform the step C include a case in which a peptide or protein as a target of pretreatment is hardly refolded after structurally subjected to reductive denaturation, and a case in which enzymatic digestion can be performed at a sufficiently high reaction rate relative to the reverse reaction. The preanalysis treatment method of the embodiment can perform enzymatic digestion at a sufficient high rection rate owing to the use of the immobilized enzyme. If the alkylation step i.e. step C is not needed, a reduction of the pretreatment time can be expected as a result of the decrease in the number of steps.

According to the preanalysis treatment method of the embodiment, as the reducing agent and the alkylating agent which is optionally used, the immobilized reagents are used, so that the subsequent treatment step or steps can be made more efficient than a case which uses non-immobilized reagents. For example, the alkylating agent reacts with the reducing agent, in many cases. Further, depending on the type of the enzyme, its enzymatic activity is reduced by the reducing agent. If the reducing agent is used as a solution, the unreacted reducing agent may hence lower the efficiency of the enzymatic reaction in the subsequent step.

According to the preanalysis treatment method of the embodiment, the use of the immobilized reducing agent can reduce the amount of the unreacted reducing agent that remains in the system, thereby enabling to make higher the efficiency of the subsequent step or steps. If the alkylating agent is used as a solution, the unreacted alkylating agent is considered to lower the efficiency of the reaction in the subsequent step, so that a quenching step is generally added. Therefore, the use of the alkylating agent in the immobilized form can reduce the amount of the unreacted alkylating agent that remains in the system, thereby making it possible to make higher the efficiency of the subsequent step or steps.

When mixing the sample and each reagent, such as the reagent A, the reagent B, or the reagent C, in the preanalysis treatment method of the embodiment, the reagent may be mixed beforehand with the below-mentioned solvent, and may then be mixed as a suspension or dispersion with the sample, although the sample and the reagent may be mixed directly.

The preanalysis treatment method of the embodiment may include a heating step, preferably a step that performs heating preferably in a range of 30° C. to 70° C. The heating step may be performed as another step from the above-mentioned steps, or may be concurrently performed with the another step by performing the above-mentioned steps under heating conditions. Preferably, the heating step is concurrently performed with at least one of the above-mentioned step A, step B, and optionally performed step C, and more preferably the step A, step B, and optionally performed step C are performed under heating conditions.

No particular limitation is imposed on a method that performs the heating step. The heating step can be performed with use of a conventional technique, for example, such as heating through thermal conduction, microwave heating, or infrared heating. The temperature i.e. heating temperature of the heating step is selected from a range where the sample and enzyme are not adversely affected, and is, for example, 30° C. to 70° C., preferably 35° C. to 60° C., more preferably 37° C. to 55° C. The heating step can be performed, for example, under normal pressure conditions, preferably, in the above-described temperature range. As an alternative, the heating step can also be performed under elevated pressure conditions. If performed under elevated pressure conditions, the temperature limit over which the enzyme loses its activity is higher than that under normal pressure conditions, so that the heating temperature range can also be set higher than the above-described temperature range in such a case.

The above-mentioned step A, step B, and optionally performed step C can be performed under shaking conditions or nonshaking conditions. For shaking, one of existing techniques including physical shaking, ultrasonic shaking, and the like can be used. No particular limitation is imposed on periods of time to be spent for the above-mentioned step A, step B, and optionally performed step C, respectively. The period of time of each step can be set short insofar as sufficient progress of the reaction is assured for the subsequent step. The reaction time in each step is, for example, 1 minute to 4 hours.

No limitations are imposed on the equivalents of the reagents to be added in the above-mentioned step A, step B, and optionally performed step C, but the reagents may be added by large excess amounts for high rate pretreatment. For example, the amount of the reducing agent contained in the reagent A may be preferably 2 equivalents to 1,000,000 equivalents, more preferably 10 equivalents to 100,000 equivalents, particularly preferably 100 equivalents to 10,000 equivalents to disulfide bonds in the sample. It is to be understood that "equivalents" means "molar equivalents." As the amount of the alkylating agent contained in the reagent C, the same ranges as those of the amount of the reducing agent contained in the reagent A can be mentioned by way of example. The content of the enzyme contained in the reagent B may be preferably 1:1,000 to 100:1, more preferably 1:200 to 50:1, particularly preferably 1:50 to 10:1 in terms of its weight ratio to the peptide or protein in the sample. In the preanalysis treatment method of the embodiment, the mixing of the reagents in the sample after the pretreatment can be reduced, so that adverse effects hardly occur on the subsequent steps even if the reagents are used in large excess amounts. Compared with the conventional sample pretreatment methods, the preanalysis treatment method of the embodiment therefore allows the amounts of the reagents i.e. the equivalents of the reagents to be increased, so that the reactions can be accelerated, and the time required for the pretreatment can be shortened.

The steps i.e. the steps X-A, X-B, and X-C, in which the reagents i.e. the reagents A, B, and C are separated from the supernatants, can be performed, for example, by use of existing techniques. Examples include natural settling, centrifugation, magnetic accumulation, sonic trapping, filtration, and the like. Two or more of these techniques may be performed in combination. Described specifically, the above-described steps X-A and X-B may each preferably include at least one method selected from natural settling, centrifugation, magnetic accumulation, sonic trapping, and filtration. Similarly, the step X-C may also preferably include at least one separation operation selected from natural settling, centrifugation, magnetic accumulation, sonic trapping, and filtration. It is to be understood that the steps X-A, X-B and X-C may be separately performed as other steps, or may be performed together as a single step.

After the step X-A, X-B, or X-C, a step of washing the separated regent A, B, or C, a step of mixing the supernatant with a washing solution resulting from the washing of the reagent, and the like may be added. On the supernatant recovered as described above, other steps may also be additionally performed before subjecting it to LC-MS measurement or the like.

A solvent may be used in the preanalysis treatment method of the embodiment. The solvent may be a water-based buffer, an organic solvent, or a mixture of a water-based buffer and an organic solvent. The solvent may contain a surfactant and/or a denaturant, although the less the use of such an additive that affects an analysis, the better. If a salt is used in a case or the like in which a water-based buffer is used, the salt may preferably be a volatile salt such as ammonium carbonate or ammonium formate, and if such a volatile salt is used, it is preferably desalted before an analysis. Preferably, the organic solvent is water-soluble such as, for example, acetonitrile or a lower alcohol.

The sample which has been treated using the preanalysis treatment method of the embodiment can be subjected to an LC-MS analysis or the like as it is or after it is subjected to appropriate treatment, such as contaminant removal, adsorption treatment, desalting, solvent replacement, dialysis, and/ or concentration, as needed. The sample treated by use of the preanalysis treatment method of the embodiment can also be subjected to an analysis other than LC-MS, such as electrophoresis or enzyme-linked immuno sorbent assay (ELISA), and no limitation is imposed on its use.

Figure 4:
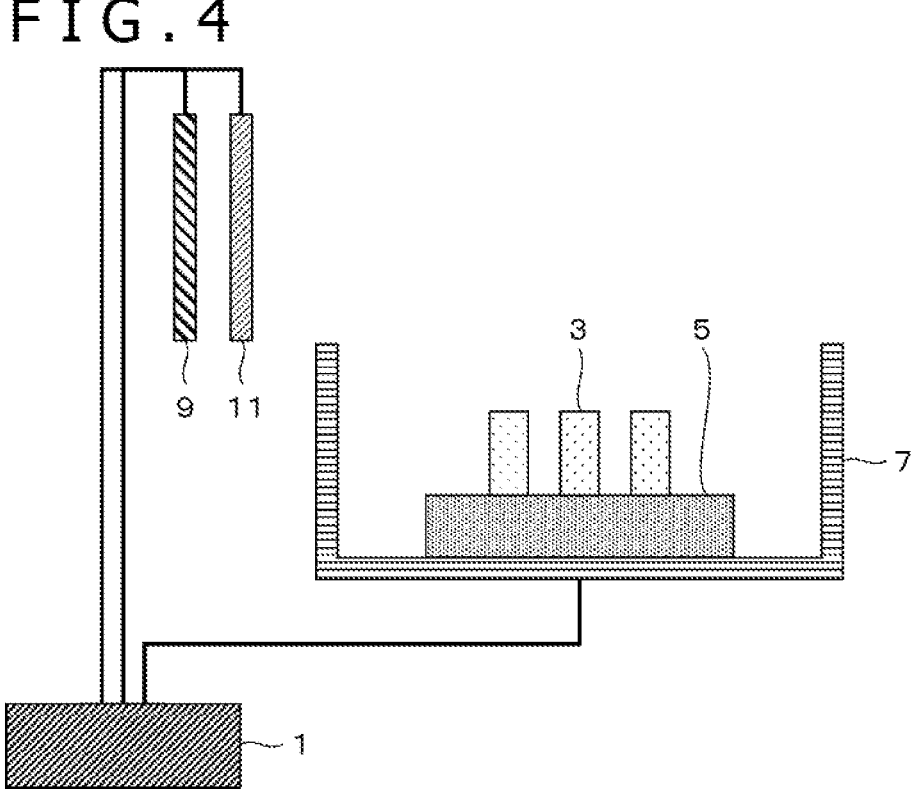
FIG. 4 is a concept diagram illustrating an aspect of a sample pretreatment system according to the embodiment.

A sample pretreatment system according to the embodiment can be any system that can perform the above-mentioned preanalysis treatment method of the embodiment. As the sample pretreatment system, there can be mentioned, for example, configurations (FIG. 4) that include, for example, a control unit 1, a sample tube rack 5, a sample tube heating/shaking unit 7, a reagent dispensing unit 9, and a supernatant recovering unit 11.

In the sample tube rack 5, a plurality of sample tubes 3 are placed. In general, samples are added to the sample tubes 3 before or after the sample tubes 3 are placed in the sample tube rack 5. The sample tube heating/shaking unit 7 is only required to heat and shake the sample tubes 3. The sample tube heating/shaking unit 7 is open at an upper part thereof in FIG. 4, but may have, for example, an openable lid. Further, the reagent dispensing unit 9 and the supernatant recovering unit 11 may be disposed in the sample tube heating/shaking unit 7. The reagent dispensing unit 9 is configured to enable addition of the reagent A, the reagent B, and the optionally used reagent C, preferably, in the forms of dispersions or suspensions to the sample tubes 3. The supernatant recovering unit 11 is only required to be configured to enable separation of the supernatants and the reagents (the reagents A, B, and C) from each other, respectively, and recovery of the supernatants, and also acts as a supernatant-reagent separation unit. No particular limitation is imposed on the sample tubes 3 in which the samples are to be held. As mentioned above, no particular limitations are imposed on the techniques to be used for the heating and shaking. Devices to be used in the reagent dispensing unit and the supernatant recovering unit to feed the reagents and the supernatants include, but are not limited to, pumps or the like. As mentioned above, no particular limitations are imposed on the techniques to be used for the separation of the supernatants and the reagents.

EXAMPLES

The embodiment will hereinafter be specifically described in Examples. However, the present embodiment should not be limited to or by the following Examples.

Example 1

In Example 1, the preanalysis treatment method of a sample was performed using a reagent A containing a support and a reducing agent immobilized thereon, a reagent B containing a support and an enzyme immobilized thereon, and a reagent C containing a support and an alkylating agent immobilized thereon.

A suspension of a phosphine-containing reducing agent immobilized on crosslinked agarose beads of 120 μm average diameter via an oligoethylene glycol-based linker (amount of the reducing agent: 0.04 mmol) (the reagent A) was added to a solution of human IgG in ABC buffer (1 wt %, 1.0 mL, approximately 0.00016 mmol as equivalent disulfide bonds), followed by heating at 55° C. for 1 hour under shaking on a Block Bath Shaker. The resulting supernatant was recovered, and was added with a suspension of an a-substituted acetamide-containing alkylating agent physically adsorbed on crosslinked agarose beads of 120 μm average diameter (amount of the alkylating agent: 0.04 mmol) (the reagent C), followed by heating at 55° C. for 30 minutes under shaking. The resulting supernatant was recovered, and was added with a dispersion of trypsin (Resyn Biosciences (Pty) Ltd.) immobilized on magnetic beads (0.08 mL) (the reagent B), followed by heating at 55° C. for 1 hour. After the resulting reaction mixture was subjected to centrifugation for 5 minutes, the supernatant was removed to separate the support and the supernatant.

The human IgG which remained in the supernatant thus obtained was quantitatively analyzed. As a result, the residual rate of undigested human IgG was calculated to be 25%. The preanalysis treatment method took approximately 2.5 hours in total.

It was demonstrated by Example 1 that human IgG can be pretreated at a high rate by reduction, alkylation, and enzymatic digestion with the reagents (immobilized reagents) which are easily separable from the supernatants and are readily usable in disposable systems.

Example 2

In Example 2, the preanalysis treatment method of the sample was performed using the reagent A, which contained the support and the reducing agent immobilized thereon, and the reagent B, which contained the support and the enzyme immobilized thereon.

A suspension of the reducing agent immobilized on magnetic beads (amount of the reducing agent: 0.08 mmol) (the reagent A) was added to a solution of human IgG in ABC buffer (1 wt %, 1.0 mL, approximately 0.00016 mmol as equivalent disulfide bonds), followed by heating at 55° C. for 1 hour under shaking on the Block Bath Shaker. After the reaction mixture thus obtained was allowed to stand for 1 minute in a vicinity of a magnet, the resulting supernatant was recovered. The supernatant was added with a dispersion of trypsin (Resyn Biosciences (Pty) Ltd.) immobilized on magnetic beads (0.08 mL) (the reagent B), followed by heating at 55° C. for 1 hour on the Block Bath Shaker. After the resulting reaction mixture was allowed to stand for 1 minute in the vicinity of the magnet, the supernatant was removed to separate the support and the supernatant.

The human IgG which remained in the supernatant thus obtained was quantitively analyzed. As a result, the residual rate of undigested human IgG was calculated to be 19%. The preanalysis treatment took approximately 2 hours in total.

It was demonstrated by Example 2 that, even when an alkylation step is not performed, human IgG can be pretreated at a high rate by reduction and enzymatic digestion with the reagents (immobilized reagents) which are easily separable from the supernatants and are readily usable in disposable systems.

Example 3

In Example 3, the preanalysis treatment method of the sample was performed concurrently using the same reagent A, which contained the support and the reducing agent immobilized thereon, and the reagent B, which contained the support and the enzyme immobilized thereon.

A suspension of the reducing agent immobilized on crosslinked agarose beads (amount of the reducing agent: 0.16 mmol) (the reagent A) and a dispersion of trypsin (Resyn Biosciences (Pty) Ltd.) immobilized on magnetic beads (0.16 mL) (the reagent B) were added to a solution of human IgG in ABC buffer (1 wt %, 1.0 mL, approximately 0.00016 mmol as equivalent disulfide bonds), followed by heating at 55° C. for 1 hour on the Block Bath Shaker. The resulting reaction mixture was drawn into a syringe, and was then separated into the supports and a supernatant through a syringe filter.

The human IgG which remained in the supernatant thus obtained was quantitatively analyzed. As a result, the residual rate of undigested human IgG was calculated to be 40%. The preanalysis treatment method took approximately 1 hour in total.

It was demonstrated by Example 3 that human IgG can be pretreated at a high rate through a step that concurrently uses the reagent A and the reagent B.

Comparative Example 1

In Comparative Example 1, the preanalysis treatment method of the sample was performed using a solution of a reducing agent, a solution of an alkylating agent, and the reagent B which contained the support and the enzyme immobilized on the support.

The reducing agent (0.04 mmol) was added to a solution of human IgG in ABC buffer (1 wt %, 1.0 mL, approximately 0.00016 mmol as equivalent disulfide bonds), followed by heating at 55° C. for 1 hour under shaking on the Block Bath Shaker. The resulting solution was recovered, and was added with the alkylating agent (0.16 mmol), followed by heating at 55° C. for 1 hour under shaking. The resulting supernatant was recovered, and was added with the reducing agent (0.08 mmoL), followed by heating at 55° C. for 1 hour under shaking. The resulting solution was recovered, and was added with a dispersion of trypsin (Resyn Biosciences (Pty) Ltd.) immobilized on magnetic beads (0.08 mL), followed by heating at 55° C. for 1 hour on the Block Bath Shaker. After the resulting reaction mixture was subjected to centrifugation for 5 minutes, the supernatant thus obtained was removed to separate the support and the supernatant.

The human IgG which remained in the supernatant thus obtained was quantitatively analyzed. As a result, the residual rate of undigested human IgG was calculated to be 65%. In addition to the high residual rate due to reductions in the activities of the reducing agent and alkylating agent as caused by their unreacted remains and byproducts, adverse effects on subsequent steps due to their mixing into the sample, especially a reduction in the sensitivity of mass spectroscopy was confirmed. The preanalysis treatment method took approximately 4 hours in total.

By Comparative Example 1, it was demonstrated that pretreatment with the non-immobilized reagents (reducing agent, alkylating agent) tends to lead to a lower efficiency, greater contaminant mixing, and a longer treatment time than pretreatment with the immobilized reagents.

By the Examples and the Comparative Example, it was also demonstrated that, compared with a sample subjected to pretreatment by either one of the conventional preanalysis treatment method, a sample subjected to treatment by the preanalysis treatment method of the embodiment can be suppressed in cross contamination because the preanalysis treatment method of the embodiment can reduce the mixing of the reagents into the sample and can facilitate to create disposable systems.

The upper limits values and/or the lower limit values of the numerical ranges described herein can individually be combined together as desired to define preferred ranges. For example, the upper limit value of one of the numerical ranges and the lower limit value of another one numerical range can be combined together as desired to define a preferred range, the upper limit values of different two numerical ranges can be combined together as desired to define a preferred range, and the lower limits values of different two numerical ranges can be combined together as desired to define a preferred range.

The claims which will follow are expressly incorporated in the disclosure described herein, and the individual claims are independent as separate embodiments. The present disclosure encompasses all of those contemplated by substituting the features of dependent claims for their corresponding features in an independent claim. Moreover, additional embodiments derived from the independent claim and its dependent claims are also expressly incorporated herein.

Persons skilled in the art can use the above-described explanation to make best use of the present disclosure. The claims and the embodiments disclosed herein are merely explanatory or illustrative, and should hence be construed not to limit the scope of the present disclosure in any sense. With the aid of the disclosure described herein, the details of the above-described embodiments can be changed without departing from the core principle of the present disclosure. In other words, various modifications and improvements of the embodiments specifically disclosed herein all fall within the scope of the present disclosure. Concerning the present invention, supplementary descriptions will be made hereinafter.

SUPPLEMENTARY DESCRIPTIONS

Supplementary Description 1

A preanalysis treatment method for a sample containing a peptide or a protein, including:
    a step A of mixing the sample and a reagent A containing a support and a reducing agent immobilized on the support;
    a step B of mixing the sample and a reagent B containing a support and an enzyme immobilized on the support;
    a step X-A of, after the step A, separating the reagent A and a supernatant from each other; and
    a step X-B of, after the step B, separating the reagent B and a supernatant from each other.

Supplementary Description 2

The preanalysis treatment method as described in the supplementary description 1, further including:
    a step C of mixing the sample and a reagent C containing a support and an alkylating agent immobilized on the support; and
    a step X-C of, after the step C, separating the reagent C and a supernatant from each other, in which
    the step C is performed between the step A and the step B.

Supplementary Description 3

The preanalysis treatment method as described in the supplementary description 1 or 2, in which
    the step A and the step B are concurrently performed, or one of the step A and the step B is performed, and the other step is then performed.

Supplementary Description 4

The preanalysis treatment method as described in any of the supplementary descriptions 1 to 3, in which the reducing agent contained in the reagent A contains at least one thiol or phosphine group as a partial structure, the enzyme contained in the reagent B is protease, and the supports each have an average diameter of 0.5 μm to 500 μm.

Supplementary Description 5

The preanalysis treatment method as described in any of the supplementary descriptions 1 to 4, further including: a step of heating in a range of 30° C. to 70° C.

Supplementary Description 6

The preanalysis treatment method as described in any of the supplementary descriptions 1 to 5, in which
the sample A contains the reducing agent in an amount of two equivalents to 1,000,000 equivalents per equivalent of disulfide bonds in the sample,
the enzyme includes at least one enzyme selected from trypsin, chymotrypsin, pepsin, Lys-C, Lys-N, and Glu-C, and
the supports each contain at least one material selected from silica, polystyrene, acrylic resins, polysaccharides, elementary metals, semiconductors, metal oxides, and magnetic metal oxides.

Supplementary Description 7

The preanalysis treatment method as described in any of the supplementary descriptions 1 to 6, in which
the steps X-A and X-B each include at least one method selected from natural settling, centrifugation, magnetic accumulation, sonic trapping, and filtration.

Supplementary Description 8

A sample pretreatment system capable of performing the preanalysis treatment method as described in any of the supplementary descriptions 1 to 7.

Supplementary Description 9

The sample pretreatment system as described in the supplementary description 8, including:
a control unit, a sample tube rack, a sample tube heating/shaking unit, a reagent dispensing unit, and a supernatant recovering unit.

What is claimed is:
1. A preanalysis treatment method for a sample containing a peptide or a protein, comprising:
a step A of mixing the sample and a reagent A containing a support and a reducing agent immobilized on the support;
a step X-A of, after the step A, separating the reagent A and a supernatant from each other;
a step C of mixing the supernatant obtained in step X-A and a reagent C containing a support and an alkylating agent immobilized on the support;
a step X-C of, after the step C, separating the reagent C and a supernatant from each other;
a step B of mixing the supernatant obtained in step X-C and a reagent B containing a support and an enzyme immobilized on the support; and
a step X-B of, after the step B, separating the reagent B and a supernatant from each other.
2. The preanalysis treatment method according to claim 1, wherein
the reducing agent contained in the reagent A contains at least one thiol or phosphine group as a partial structure,
the enzyme contained in the reagent B is protease, and
the supports each have an average diameter of 0.5 μm to 500 μm.
3. The preanalysis treatment method according to claim 1, further comprising:
a step of heating in a range of 30° C. to 70° C.
4. The preanalysis treatment method according to claim 1, wherein
the reagent A contains the reducing agent in an amount of two equivalents to 1,000,000 equivalents per equivalent of disulfide bonds in the sample when added in step A,
the enzyme includes at least one enzyme selected from trypsin, chymotrypsin, pepsin, Lys-C, Lys-N, and Glu-C, and
the supports each contain at least one material selected from silica, polystyrene, acrylic resins, polysaccharides, elementary metals, semiconductors, metal oxides, and magnetic metal oxides.
5. The preanalysis treatment method according to claim 1, wherein
the steps X-A and X-B each include at least one method selected from natural settling, centrifugation, magnetic accumulation, sonic trapping, and filtration.

* * * * *